United States Patent
DeLuca et al.

(10) Patent No.: US 8,454,624 B2
(45) Date of Patent: Jun. 4, 2013

(54) DEVICE FOR REMOVING A LODGED MASS

(76) Inventors: James T. DeLuca, Forrest Hills Gardens, NY (US); Paul V. DeLuca, Palm City, FL (US)

(*) Notice: Subject to any disclaimer, the term of this patent is extended or adjusted under 35 U.S.C. 154(b) by 286 days.

(21) Appl. No.: 12/932,508

(22) Filed: Feb. 25, 2011

(65) Prior Publication Data

US 2012/0221010 A1    Aug. 30, 2012

(51) Int. Cl.
*A61D 1/12* (2006.01)

(52) U.S. Cl.
USPC ......... 606/106; 604/77; 604/317; 128/200.23

(58) Field of Classification Search
USPC ................... 606/106; 604/317, 77, 346, 319, 604/1, 2, 18, 289, 416, 540, 73, 181, 35, 604/36, 37, 38; 128/200.23, 201.23, 201.26, 128/205.22, 202.26, 207.14–207.18, 206.28, 128/206.29, 205.18; 228/20.5, 20.1; 137/625.69, 625.34, 625.35; 15/345; 43/110; 600/565
See application file for complete search history.

(56) References Cited

U.S. PATENT DOCUMENTS

| | | | | |
|---|---|---|---|---|
| 3,665,919 A * | 5/1972 | Laerdal | ...................... | 604/149 |
| 3,939,830 A * | 2/1976 | da Costa | ................... | 128/205.18 |
| 3,980,218 A * | 9/1976 | Fortune | ...................... | 228/20.5 |
| 4,790,818 A * | 12/1988 | DeLuca et al. | ................. | 604/540 |
| 4,971,053 A * | 11/1990 | Tarrats | ..................... | 128/205.19 |
| 5,609,149 A * | 3/1997 | Takach | ..................... | 128/200.24 |
| 5,782,837 A * | 7/1998 | York | ............................ | 606/106 |
| 6,478,770 B1* | 11/2002 | Litkouhi et al. | ................. | 604/77 |
| 7,351,245 B2* | 4/2008 | Rozinsky et al. | ............. | 606/106 |
| 7,559,921 B2* | 7/2009 | DeLuca et al. | ................. | 604/317 |
| 2003/0028158 A1* | 2/2003 | Litkouhi et al. | ................ | 604/319 |
| 2006/0064111 A1* | 3/2006 | Rozinsky et al. | ............. | 606/106 |
| 2006/0161170 A1* | 7/2006 | DeLuca et al. | ................. | 606/106 |
| 2009/0228018 A1* | 9/2009 | Winiarski | ..................... | 606/106 |

\* cited by examiner

*Primary Examiner* — Gary Jackson
*Assistant Examiner* — Katrina Stransky
(74) *Attorney, Agent, or Firm* — Thomas A. O'Rourke; Bodner & O'Rourke, LLP (57) ABSTRACT

A device for removing a mass lodged in a choking victim's throat comprises a manifold, piston, spool, and latch. The manifold has first, second, and third conduits in selective fluid communication with each other, with the second conduit terminating in an orifice in a mouthpiece. The spool, having a transverse orifice, may be disposed in the third conduit, slidable between a first position where the orifice permits fluid communication between the first and second conduits, and a second position where the spool blocks fluid communication. The piston is slidably disposed within the first conduit, and with the spool is in the second position, the latch is usable to secure the piston relative to the manifold at one or more discrete positions to create a measured amount of vacuum pressure in the first conduit. The vacuum pressure is transmitted to the mouthpiece by movement of the spool to said first position.

25 Claims, 12 Drawing Sheets

DEVICE FOR REMOVING A LODGED MASS

FIELD OF THE INVENTION

This invention relates to anti-choke devices employed for removing a mass or bolus lodged in the throat of a victim, and more particularly, to a device which is capable of improved reliability and ease of use, while being produced at a relatively modest cost.

BACKGROUND OF THE INVENTION

Unintentional injury has been a leading cause of death among people aged 1 to 44, and has been the fifth leading cause of death overall in the United States. In a 2004 report, unintentional injuries at home resulted in nearly 20,000 deaths and 21 million medical visits, with death from choking and suffocation ranked fourth among the cause of unintentional home injury. In addition to home choking incidents, where for children there are generally at least as many resulting from ingested toys as for food products being eaten, there are many choking incidents occurring at restaurants and other locations.

Medical devices being usable to affect the respiration of a patient or a person in distress may be found dating back very early in the art, including, for example, the 1919 "Respirating Device" of U.S. Pat. No. 1,371,702 to Lyon. But these early devices were adapted to provide a mechanical means of stimulating artificial respiration by causing lung movement through the introduction of air and/or oxygen flowing thereto and therefrom, in correspondence with the normal capacity of the person's lungs. However, such devices eventually were adapted to provide a means of supplying a negative pressure to a person's airway in order to induce the removal of a mass of food lodged therein, to relieve choking and prevent death, which occurs frequently in such cases.

One such device is found in U.S. Pat. No. 4,971,0533 to Tarrats for a "Suction Mask to Relieve Choking." The Tarrats device comprises a moveable piston disposed within a cylinder, and with an airway in communication with the cylinder and extending through a mask that is sealable upon a victim's mouth. The piston is spring loaded to drive it to one end of the cylinder. The spring biasing may be overcome manually to move the piston into a ready position, where it may be releasably secured using a pivotable lever. When a choking victim requires assistance, the airway of the device may be inserted into his/her throat, with the mask sealing upon the person's face, and when the lever is released, the spring drives the piston to the opposite end of the cylinder, creating a vacuum to draw out the mass of food from where it is lodged. However, one major drawback of the Tarrats device is that the vacuum pressure must build up over time as the piston moves within the cylinder. Removal of a lodged mass is far more effective when a sustained vacuum pressure may be applied instantaneously.

Another drawback of the Tarrats suction device is the method of attempting to control the amount of air in the chamber, so as to be appropriate for the size of the victim. Tarrats uses a spring biased lever mounted to the housing that may engage a each of series of square grooves, but this requires that the good Samaritan seeking to use the device on a victim or the victim seeking to use the device upon themselves must simultaneously hold the device while depressing the lever to release the piston, to then pull the piston from the chamber to create the vacuum pressure. The awkwardness of the arrangement would hamper operation of the device in the typical choking scenario where the speed in using and possibly reusing the device a second time are critical for the health and life of the victim. This awkward arrangement furthermore does not correlate the stroke of the piston with the volume of vacuum pressure created, so as to inform the user that the piston is properly positioned for that particular sized choking victim.

Similarly, U.S. Pat. No. 5,609,149 to Takach discloses an "Anti-Choke Device" in which a plunger is manually driven to create a vacuum pressure, but where the plunger is resilient and flexible to be responsive through deflection to prevent excessive vacuum, and thereby prevent injury such as a collapsed lung. However, Takach states that "a swift depression of the plunger induces strong partial vacuum which is useful in clearing a lodged obstruction from the throat." Therefore, Takach suffers from the same drawback as Tarrats, in that the vacuum is not instantaneously applied, and conversely relies upon "swift" action by the person striving to provide aid to the choking victim.

U.S. Pat. No. 6,478,770 to Litkouhi, discloses a device that significantly improves upon the prior art by utilizing a sealed vacuum container as a source of negative pressure in creating an instantaneous and sustained pressure drop "to overcome the forces of weight and frictional engagement between the bolus and the contiguous tissue against which the bolus is lodged." Although the device is very well adapted to serve effectively in removal of a lodged mass by a person carefully rendering the aid, where an attempt to operate the device is rushed and/or performed clumsily such that the attempt to dislodge the mass is unsuccessful, ready access to another vacuum canister is required to repeat the procedure. A second replacement canister may not be readily available, and may not be easily inserted in the device in order to repeat the procedure. Also, it may be appreciated that a canister being installed within a device may lose vacuum pressure when it is stored for a significant time, and may thus require periodic inspections and/or servicing. The device of the present invention provides improvements and advantages over the prior art as hereinafter described.

OBJECTS OF THE INVENTION

It is an object of the invention to provide a device being usable to deliver vacuum pressure to the throat of a choking victim to remove a mass lodged therein.

It is another object of the invention to provide a vacuum removal device being quickly adaptable for use on a choking victim of any size, ranging from as small as a baby to as large as a seven-foot tall basketball player.

It is a further object of the invention to provide a vacuum removal device being easily set-up for use, so as to permit repeated use where a lodged mass was not removed on an initial attempt.

It is another object of the invention to provide a vacuum removal device that incorporates replaceable mouthpiece elements, to permit a new mouthpiece to be utilized on successive victims.

It is also an object of the invention to provide a means of delivering instantaneous vacuum pressure to the throat of a choking victim.

Further objects and advantages of the invention will become apparent from the following description and claims, and from the accompanying drawings.

SUMMARY OF THE INVENTION

A suction device being usable for the vacuum removal of a lodged mass from the throat of a victim is disclosed herein.

The device may comprise a manifold, a spool, a piston, and a latch. The manifold may comprise first, second, and third conduits that may selectively be in fluid communication with each other.

The second conduit may terminate at one end in an outlet orifice in a mouthpiece portion of the manifold—a mouthpiece which may be replaceable so as to permit use of a clean mouthpiece with subsequent usage of the device upon a different choking victim. The other end of the second conduit may interconnect with the first conduit. The third conduit may have a first end and a second end, with the third conduit being transverse to the interconnecting portion of the second conduit. A spool may be slidably disposed in the third conduit and be moveable between a first position, where an orifice therein permits fluid communication between the first conduit and the second conduit, and a second position where the orifice is no longer in line with the interconnection, and the spool blocks fluid communication therebetween. The spool may be spring biased to be in the second spool position. The spool may generally be a cylindrical member, but other cross-sectional shapes may alternatively be used with a corresponding third conduit shape. The manifold may include a second orifice in the outer wall into the first end of the third conduit, so that the spool may be movable therein using a portion of the spool protruding out of the second manifold orifice. A knob may be affixed to the protruding portion of the spool to aid a caregiver in activating the device.

The piston may be slidably disposed within the first conduit, and may be moveable therein between a first end and a second end of the first conduit, and may include one or more O-rings to help provide a more leak-resistant chamber to create and secure the vacuum needed to draw the lodged mass from the victim's throat. An orifice in an outer wall of the manifold may interconnect into the first end of the first conduit and may thus permit a portion of the piston to protrude out of the manifold through the orifice. The protruding portion of the piston may be usable by an aid giver to manually move the piston. To aid in its utility in moving the piston, the protruding portion may terminate in an elongated ring shape that is ergonomically formed to be grasped by the caregiver's hand, to be more conducive in applying a load to produce a suitable vacuum within the first conduit, when the spool remains biased in the second position. The piston may be securable relative to the manifold through the use of a latch, to maintain the vacuum within the conduit.

The latch may comprise a tab on a portion of the piston that has exited the manifold. The tab may be biased to protrude laterally relative to the rest of the piston so as to engage the manifold once the piston is moved sufficiently for the tab to exit the first conduit at the manifold orifice. One or more such tabs may be located on the piston. As an alternative to the tabs, the latch may comprise a series of holes on the piston, and a spring biased rocker arm or pin being pivotally attached to the manifold to be in line with the series of piston holes so as to deflect out of each of the holes when the piston is being moved. The piston may be moved to a specific location to create a measured amount of vacuum pressure. The spring biased rocker arm may engage one of the series of holes, once the measured amount of vacuum pressure has been created, and the user stops applying a force to the piston handle. A series of labels relating the size of the victim to a preferred amount of vacuum pressure may guide the first aid giver in determining which of the series of holes to select to create the measured amount of vacuum.

With the spool in the second position, and with the piston moved and latched to create a measured amount of vacuum pressure in the first conduit, the mouthpiece portion of the device may be inserted into the mouth of the victim, and sealed thereon. The vacuum pressure may then be transmitted into the victim's mouth and through his/her esophagus to dislodge the mass causing choking therein, by moving the spool to the first position. Using the knob on the spool to cause its movement from the second position to the first position may serve to provide a more instantaneous application of the vacuum to the victim, with increased chances or removal of the mass on the first attempt. However, the device is adapted for its ease of set-up and use, to thereby permit repeated application of vacuum pressure, if needed.

BRIEF DESCRIPTION OF THE DRAWINGS AND TABLES

Table 1 provides a comparison of values of the pressure chamber volume for various stroke amounts of a piston whose area is 1.53 inches.

DETAILED DESCRIPTION OF THE INVENTION

Figure 8:
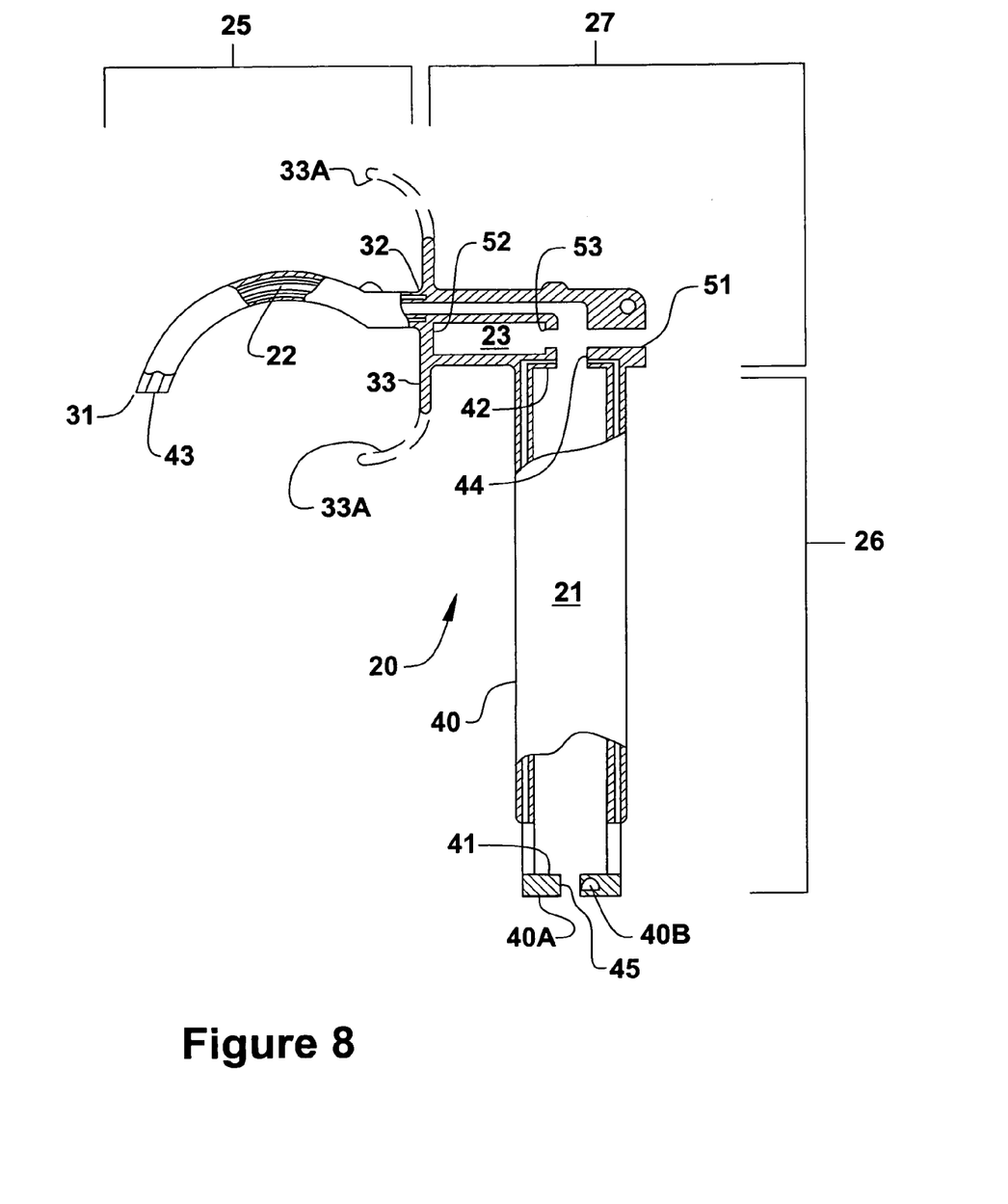
FIG. 8 is a side cross-sectional view of the manifold of the device of FIG. 1.

A suction device 10 (FIG. 1) being usable for the vacuum removal of a lodged mass from the throat of a victim is disclosed herein. The device 10 may comprise a manifold 20, with a spool 60, and a piston 80 being operable therein. One embodiment of the manifold 20 is shown in FIG. 8. The manifold may be considered to be comprised of three separate portions—a mouthpiece portion 25, a pressure chamber portion 26, and a governor portion 27, and may also have three conduits located therein, a first conduit 21, a second conduit 22, and a third conduit 23. Most of the elements of the device may be formed by injection molding techniques of synthetic resinous material known in the art, or other suitable manufacturing techniques, including, but not limited to, castings, forgings, machinings, etc.

The mouthpiece portion 25 may be curved to permit its insertion into the victim's mouth, so as to be able to circumvent the tongue to reach the throat, and may thus be able to prevent the tongue from blocking the oropharyngeal airway, and from blocking the transmission of the vacuum pressure to the lodged object. The mouthpiece portion 25 of the manifold 20 in FIG. 8 may have a first end 31, and a second end 32. Where the second end 32 of the mouthpiece portion joins the governor portion 27 of the manifold 20, there may be a sealing means 33 usable for sealing the device against the face of the victim, to prevent the vacuum pressure from being countered by a rush of air that is in proximity to the victim's mouth. Sealing means 33 may generally be a flexible disk that may be sealable against the victim's lips. Sealing means 33 may alternatively further comprise a curved portion 33A to form a mask that may flexibly fit over the victim's mouth and nose to also prevent a rush of air through the nasal passageway from weakening the effects of the applied vacuum pressure.

The governor portion 27 of manifold 20 may protrude orthogonally from the sealing means 33, while the pressure chamber portion 26 may protrude orthogonally from the governor portion 27, to create a device 10 that may be ergonomically configured for an aid-giver trying to insert and utilize the device with respect to a victim.

Figure 3:
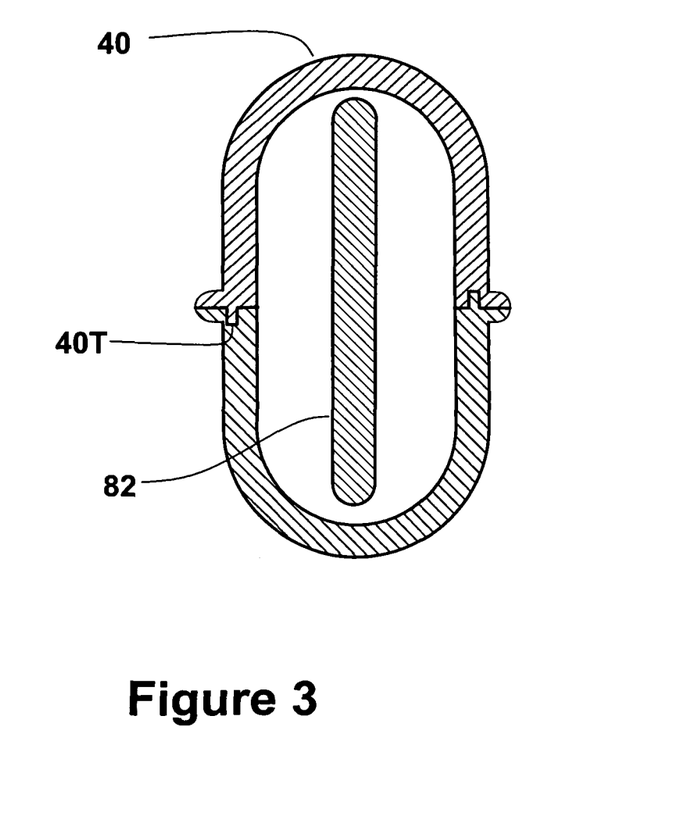
FIG. 3 is a cross-sectional view taken normal to the axis of the pressure chamber portion of the device of FIG. 1.
Figure 18:
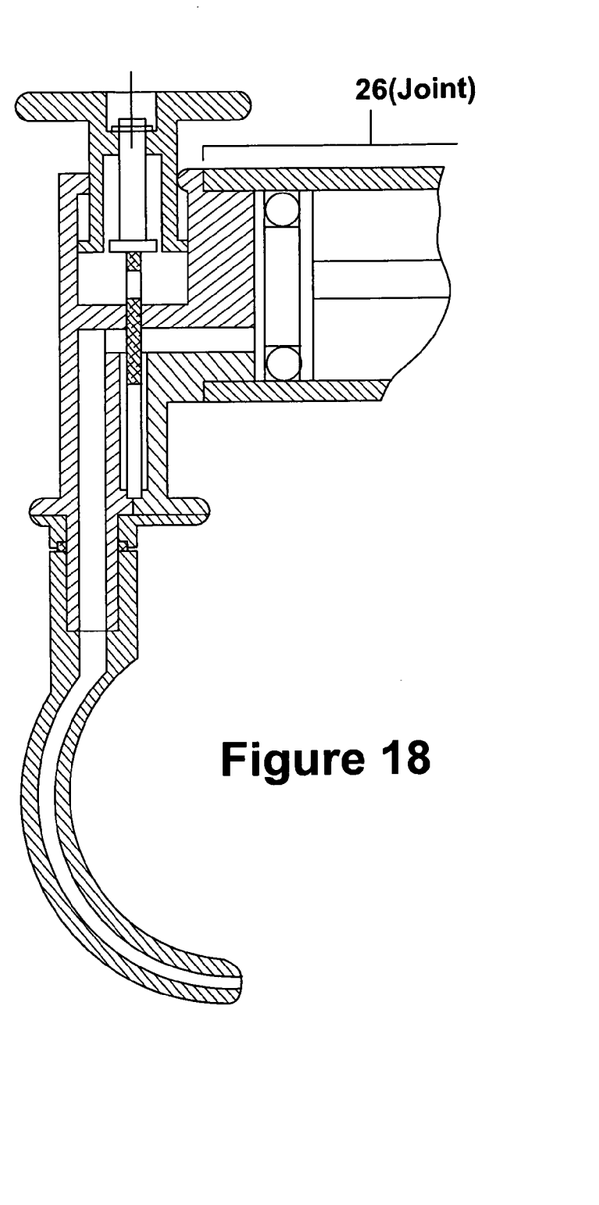
FIG. 18 is a front cross-sectional view through the device of FIG. 17.

The pressure chamber portion 26 may be integrally formed with the rest of manifold 20, or may be a separate piece that may be attached to the governor portion 27 of the manifold 20 using male/female threading, bonding, welding, or any other suitable attachment technique (see FIG. 18). The pressure chamber portion 26 may comprise an exterior wall 40 that may be any suitable shape, including being cylindrically-shaped, but is shown in the figures, merely to be illustrative, as having a race-track shape. The figures also illustrate the possibility of the manifold being constructed from two pieces, and of it being joined using a tongue and groove joint 40T (FIG. 3), although other joint types may also be used, including a butt joint, miter joint, lap joint, box joint, dovetail joint, etc. The joint may be secured using epoxy, or any other suitable means known in the art for permanently securing the joint to resist leakage, including, but not limited to, percussive welding of the parts.

The end of the pressure chamber portion 26 that is distal from the governor portion 27 may comprise a wall 40A, which may be a flat end wall, or which may alternatively be a semi-spherically-shaped wall. The wall 40A may have an opening 45 therein. The interior of the pressure chamber portion 26 may comprise a chamber or first conduit 21, which may have a shape paralleling and corresponding to the exterior of the wall 40—being race-track shaped in the figure. The first conduit 21 may extend from a first end 41, being at the interior of end wall 40A, to a second end 42 where the pressure chamber portion 26 joins the governor portion 27.

A second conduit 22 may begin at a first end of the mouthpiece portion 25 as an outlet orifice, and may continue all the way through the mouthpiece portion and through the governor portion 27. Within the governor portion 27, second conduit 22 may turn and continue on so as to interconnect, at a second end 44, with the first conduit 21 in the pressure chamber portion 26, so as to be in fluid communication therewith.

A third conduit 23 may be located within the governor portion 27 of the manifold 20 to be transverse to the interconnecting end 44 of the second conduit 22, and may be in fluid communication therewith. A first end 51 of the third conduit 22 may create an orifice in the manifold wall, while a second end 52 of the third conduit may be in proximity to the opposite side of the manifold, but does not pierce the wall and does not create an orifice. Part way between the first end 51 and the second end 52, there may be a change in the size of the third conduit 22, which may be any suitable cross-sectional shape, including rectangular, circular, racetrack-shaped, etc. Where a circular cross-section is used to create a cylindrical conduit, the diameter of the portion of the conduit at the first end 51 may be smaller than the diameter of the conduit at the second end 52, creating a shoulder 53.

Figure 1:
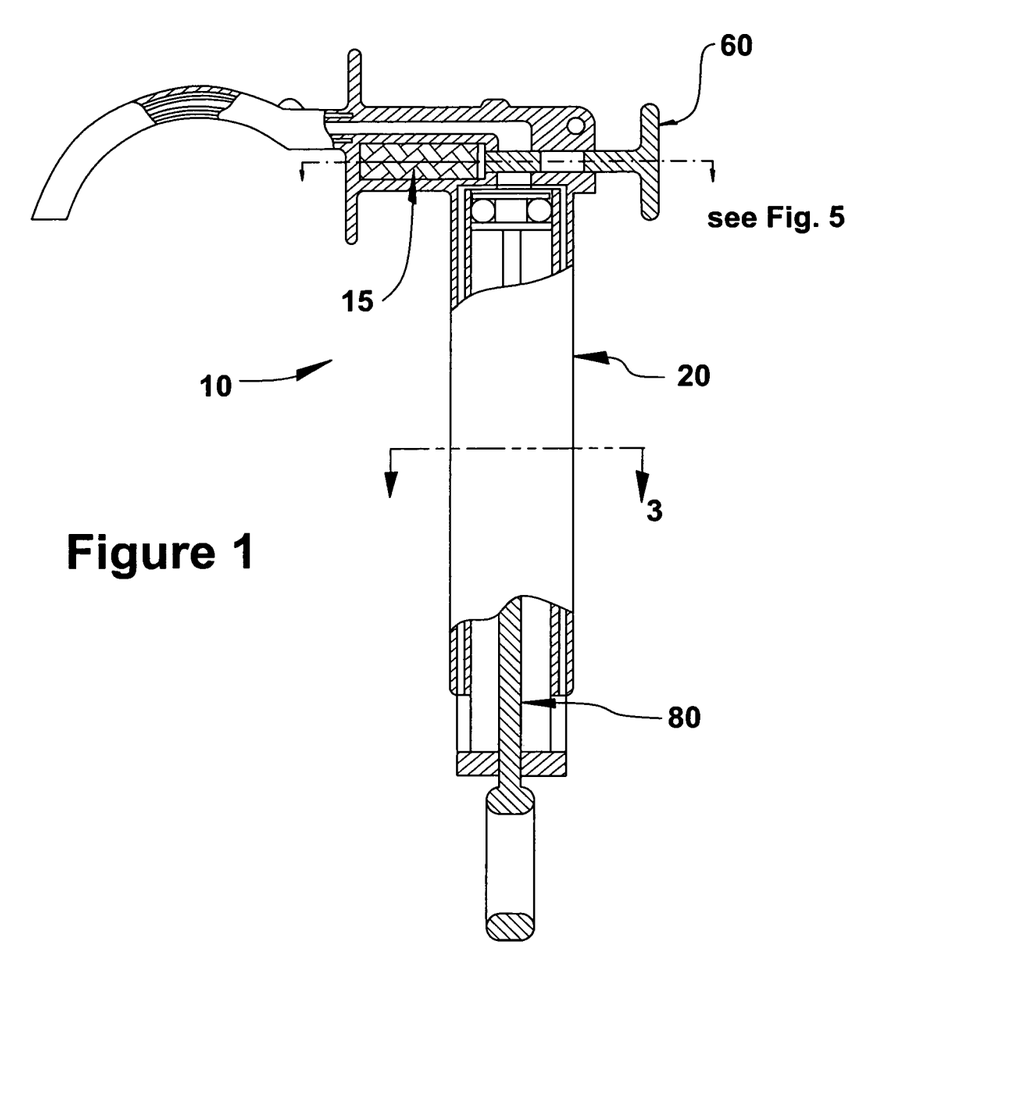
FIG. 1 is a side cross-sectional view through a first embodiment of the device of the present invention for removing a lodged mass from a victim's throat.
Figure 2:
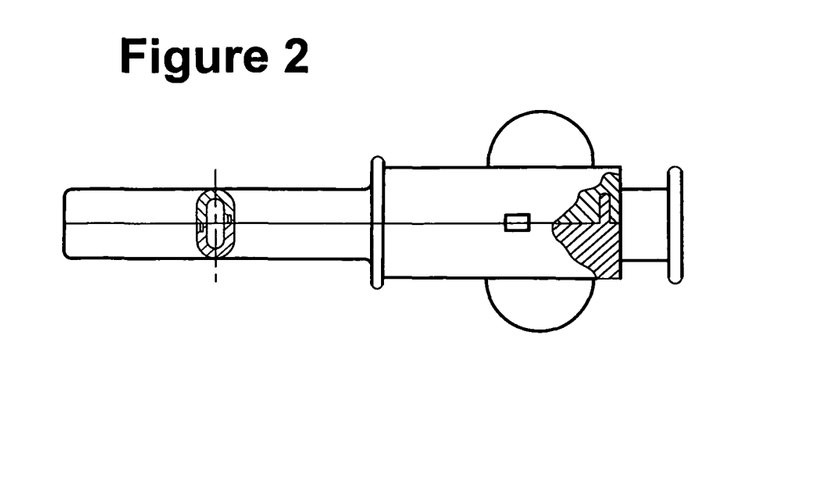
FIG. 2 is a top view of the device of FIG. 1.
Figure 9:
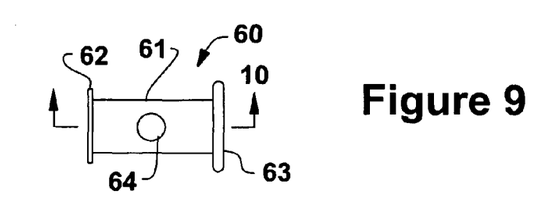
FIG. 9 is a top view of the spool of the present invention.
Figure 10:
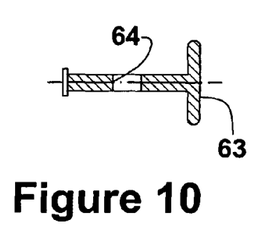
FIG. 10 is a cross-section through the spool of FIG. 9.
Figure 11:
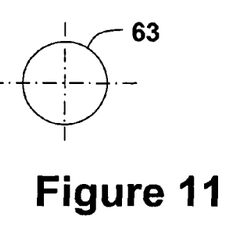
FIG. 11 is an end view of the cap of the spool of FIG. 9.

Disposed within the third conduit 23 of the governor portion 27 may be spool 60, which is seen in detail in FIGS. 9-11, and as installed in FIG. 1. The spool 60 may comprise a shaft 61 which may be cylindrical, rectangular, or an elongated ovoid shape. The shaft 61 may have an orifice 64 located therein at a position that may control fluid communication between the conduits, as discussed hereinafter. The spool 60 may also comprise a disk-shaped knob 63 on one end, and a protruding stop 62 at the other end of the spool.

The spool may be slidably disposed in the third conduit 23 (FIG. 1), and be biased therein by a spring 15, which may be a compression spring. The spring 15 may be pre-loaded so as to be in contact with the stop 62 to bias the spool 60 from a first position, where orifice 64 permits fluid communication between the first conduit 21 and the second conduit 22, to a second position, where the stop contacts the shoulder 53 of the manifold, and the spool blocks fluid communication between the first and second conduits. A portion of the spool shaft 61 may protrude out of the manifold orifice 51 thereby making the knob 63 of the spool accessible to an aid giver seeking to use the device on the victim itself.

Figure 12:
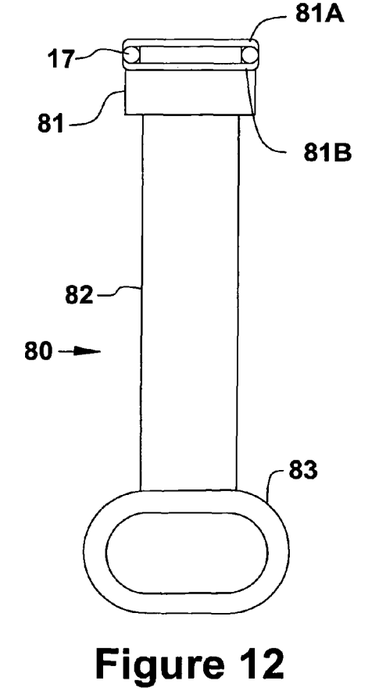
FIG. 12 is a front view of the piston of the current invention.
Figure 13:
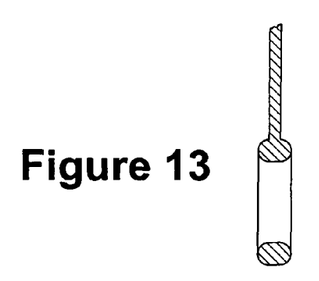
FIG. 13 is a cross-sectional view of the handle portion of the piston of FIG. 12.
Figure 14:
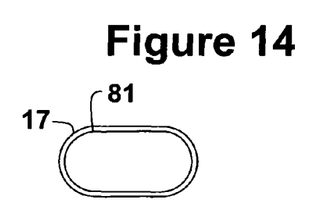
FIG. 14 is an end view of the piston of FIG. 12.

Disposed within the first conduit 21 may be the piston 80, which is seen in detail in FIGS. 12-14, and as installed in FIG. 1. The piston 80 may comprise a piston portion 81, a shaft portion 82, and a handle portion 83. The piston portion 82 may preferably be shaped to correspond to the interior shape of the first conduit 21, which in the figures is illustrated to be a race-track shape. The size of the piston portion 82 may be such that it is slidable within the first conduit 21 using a very close clearance fit so as to be generally leak-resistant as to any fluid seeking to permeate therebetween. Alternatively, the clearance fit may not be quite as close, and a flexible O-ring 17 being adapted for use in vacuum applications may be secured between first and second flanges 81A and 81B of the piston portion 81, to provide fluid leak resistance between the piston 80 and the manifold 20. The shaft portion 82 may extend from the piston portion 81, a distance being sufficient to correspond to the length of the first conduit 21, as discussed hereinafter.

Figure 4:
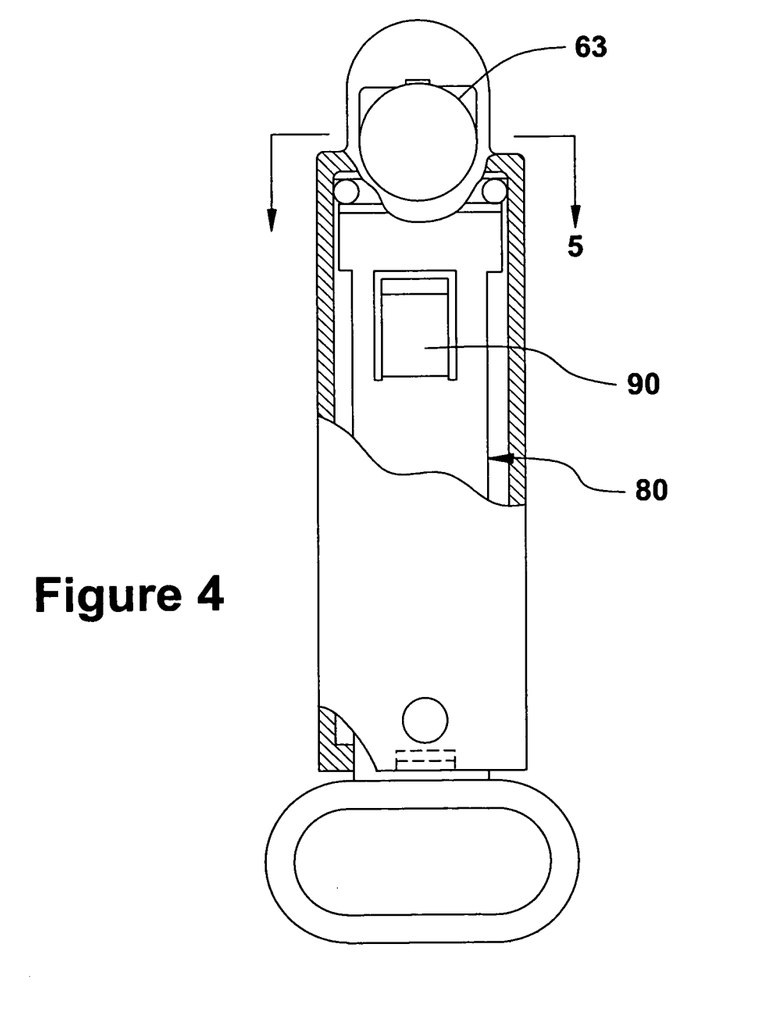
FIG. 4 is a cross-sectional view taken along the axis of the pressure chamber portion of the device of FIG. 1, shown with the piston retracted into the tube.
Figure 5:
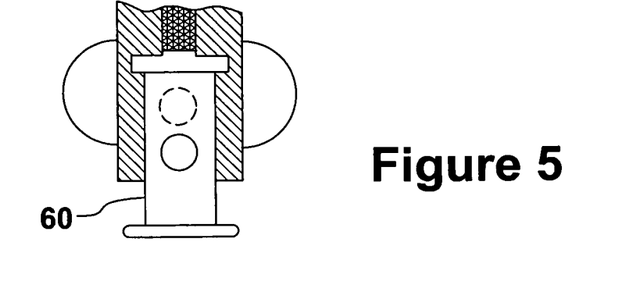
FIG. 5 is a cross-sectional view through the device of FIG. 1, taken along the axis of the spool.

The piston 80 may be slidably disposed within the first conduit 21 to have the piston portion 81 be moveable therein between the first end 41 and the second end 42 of the first conduit. The shaft 82 may protrude out of opening 45 of wall 40A of the manifold 20. The shaft 82 may be of sufficient length so that the piston portion 81 of piston 80 may be located in the first conduit 21 so as to be in contact with the second end 42 (FIGS. 1 and 4), with the shaft nonetheless protruding out from opening 45 of wall 40A of the manifold 20 to permit a user of the device to grasp the handle portion 83 in order to be able to slide the piston to cause it to then be in contact with the first end 41 of the first conduit (FIG. 6).

The shaft 82 may contain a latch in order to secure the piston 80 relative to the manifold 20 when the piston is moved from the second end 42 of first conduit 21 towards the first end 41 to create vacuum pressure therein. As seen in FIGS. 6 and 7, a first embodiment of the latch may comprise a tab 90 at one or more locations on the piston shaft 82, with the tab 90 being biased to protrude laterally with respect to the rest of the shaft. So, as a user applies a force to the handle 83 to move the piston toward the first end 41, once the tab 90 exits the orifice 45 of wall 40A of manifold 20, the tab 90 will deflect laterally and engage the manifold when the user ceases to apply pressure to the piston handle 83. The tab 90 may engage a recess 40B, as seen in FIGS. 7 and 8.

It is known in the relevant medical field that lung capacities vary among individuals of different ages and sizes. The field of Spirometry uses pulmonary function tests to make various measurements as to the amounts of air that may be inspired and/or expired by a person. One such measurement is the forced expiratory volume achieved in one second of time ($FEV_1$), which has been found, for individuals of different heights between 46 to 74 inches, to range between 0.79 liters and 5.79 liters. This $FEV_1$ range illustrates that using the same or even nearly the same amount of vacuum pressure for a four foot tall person and a six foot tall person could on one hand be totally ineffective, and on the other hand could be potentially damaging to the choking victim's lungs. Therefore, it is highly desirable to create a measured amount of vacuum pressure in the first conduit to be appropriate for use on a particular sized victim.

Figures 6, 7:
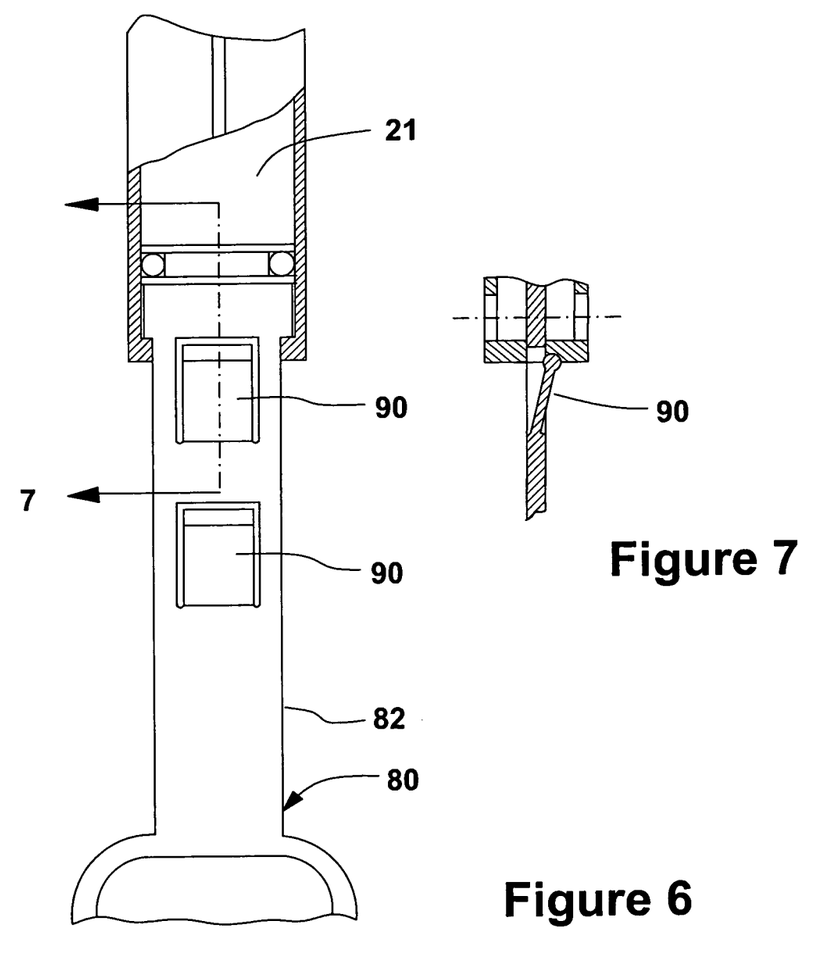
FIG. 6 is a cross-sectional view along the axis of the pressure chamber portion of the device of FIG. 1, shown with the piston moved to create a vacuum and latched to the manifold.
FIG. 7 is a side view of the latch of FIG. 6, with a tab of the latch biased into position to engage a recess on the manifold.
Figure 6A:
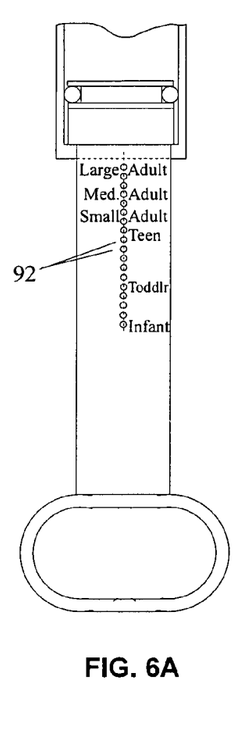
FIG. 6A is the cross-sectional view of FIG. 6, shown being latched to the manifold using an alternate embodiment of the latch.
Figure 6B:
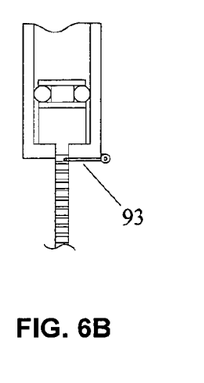
FIG. 6B is a side view of the alternate embodiment of FIG. 6A.
Figure 7A:
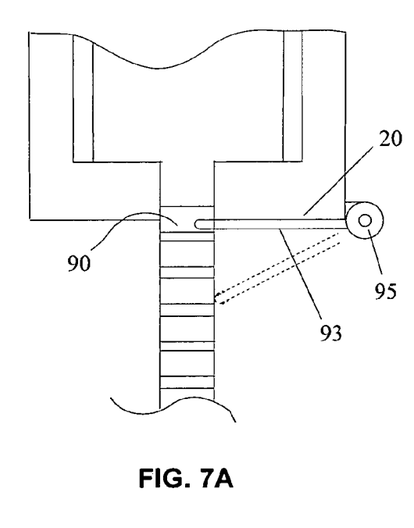
FIG. 7A is a side cross-sectional view of the alternate latch embodiment of FIG. 6A.

As seen in FIG. 6, a series of tabs 90 may be disposed along the length of the shaft, thereby permitting the aid-giver to select the amount of vacuum pressure to be used in attempting to dislodge the food mass or other object stuck within the choking victim's throat. An alternative embodiment being adapted to provide a measured amount of vacuum pressure is shown in FIGS. 6A and 7A. Instead of tab 90, a series of holes 92 may be disposed in the shaft 82 of the piston 80 at selected locations along the length of the shaft, so that as the piston shaft is moved to create vacuum pressure, successive holes may protrude from orifice 45 of manifold 20. The holes 92 may each be labeled, as seen in FIG. 6A, to provide an indication to the user of the device, as to the appropriate amount of piston displacement necessary to create the desired (measured) amount of vacuum pressure for a particular sized victim.

Table 1 illustrates the differences in volume of vacuum pressure created for various displacements of the piston. An engagement pin 93 may be pivotally mounted to the manifold 20, and be biased towards the manifold by a torsion spring 95, so that as the piston shaft 82 exits the manifold, the pin 93 will be pushed away from the manifold when it catches on hole 92. The pin may be kept from being trapped within the hole and conversely may permit outward movement of the piston shaft by having the hole 92 diameter being oversized relative to the diameter of pin 93.

Once the piston shaft 82 has exited to the point where the hole's description (large adult, medium adult, small adult, teen, . . . toddler, . . . infant) matches the victim's size (e.g., the chosen stroke correlates to a volume of air suitable for a young adult), the aid giver may stop applying a force to the handle. As the piston shaft tends to retract within the first conduit 21 due to the measured amount of vacuum pressure built up therein by displacement of the piston, the pin 93 may engage the nearest one of the series of holes 92 and prevent further backward movement of the piston shaft due to the vacuum pressure, by simultaneously bearing, on the one side, against the hole 92, and bearing on the other side against the manifold 20. The head of the pin 93 may be rounded and polished to prevent it from jamming against the shaft 82, which may similarly be smooth and polished.

Figure 15:
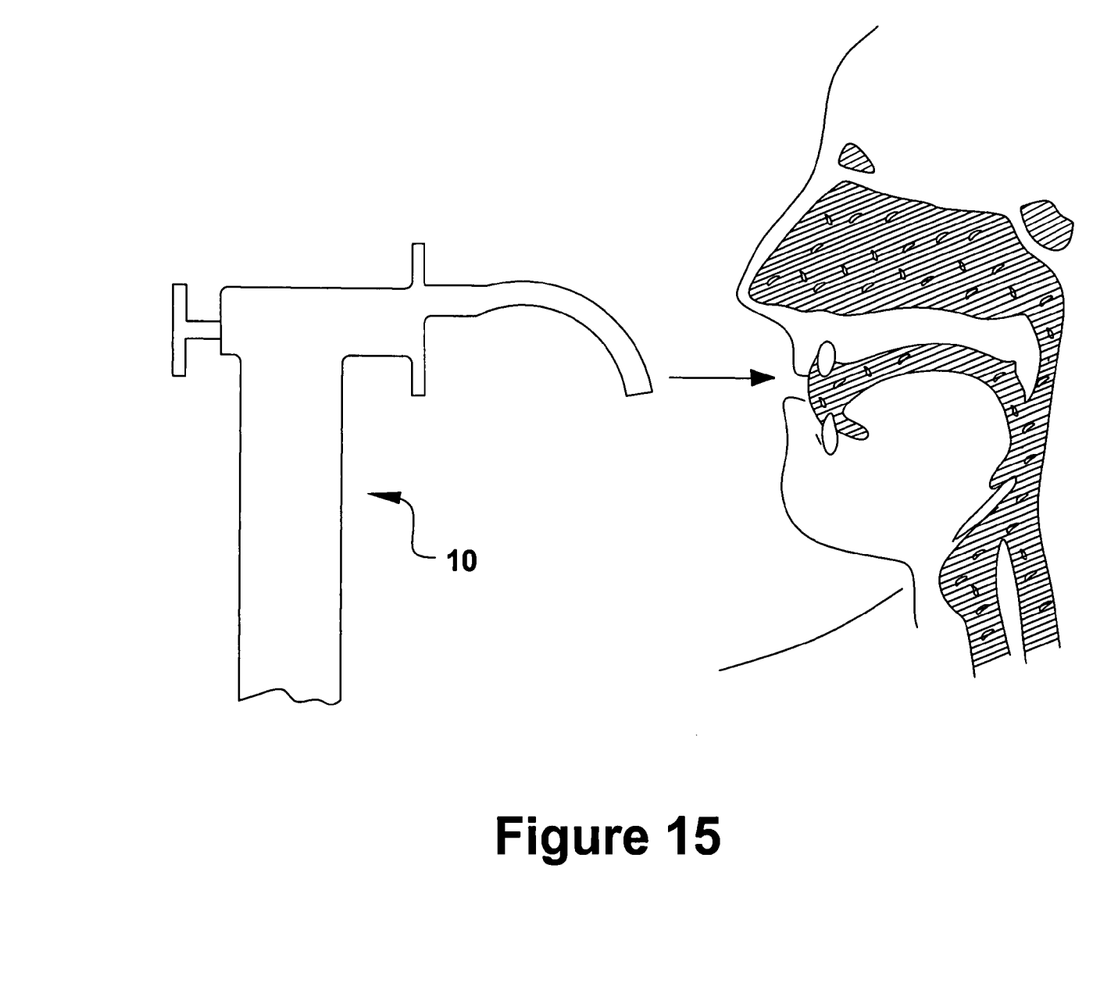
FIG. 15 is a view of the device of the present invention prior to being inserted into the throat of a choking victim.

With the spool 60 having been biased to block the interconnection between the first and second conduits and with the piston 80 moved and latched to create a measured amount of vacuum pressure within the first conduit 21, the mouthpiece portion 25 may be properly inserted into the mouth of the victim and sealed thereon using the sealing means 33. FIG. 15 illustrates a side view of the device 10 prior to insertion of the device's mouthpiece through the mouth and around the tongue of a choking victim. Once placed in the victim's throat and secured against the victim's mouth, the aid giver may then use the knob 63 to advance the spool 60 from the second position to the first position, so the measured amount of vacuum pressure in the first conduit 21 is transmitted through the spool orifice 64 into the second conduit 22 and to the outlet orifice 43 of the mouthpiece to dislodge the item causing the victim to choke. Should the procedure fail to dislodge the item, the procedure may be quickly repeated using the device herein, and may be done so with an incrementally higher amount of vacuum pressure by advancing the piston shaft to the next hole 92 in the series.

Figure 16:
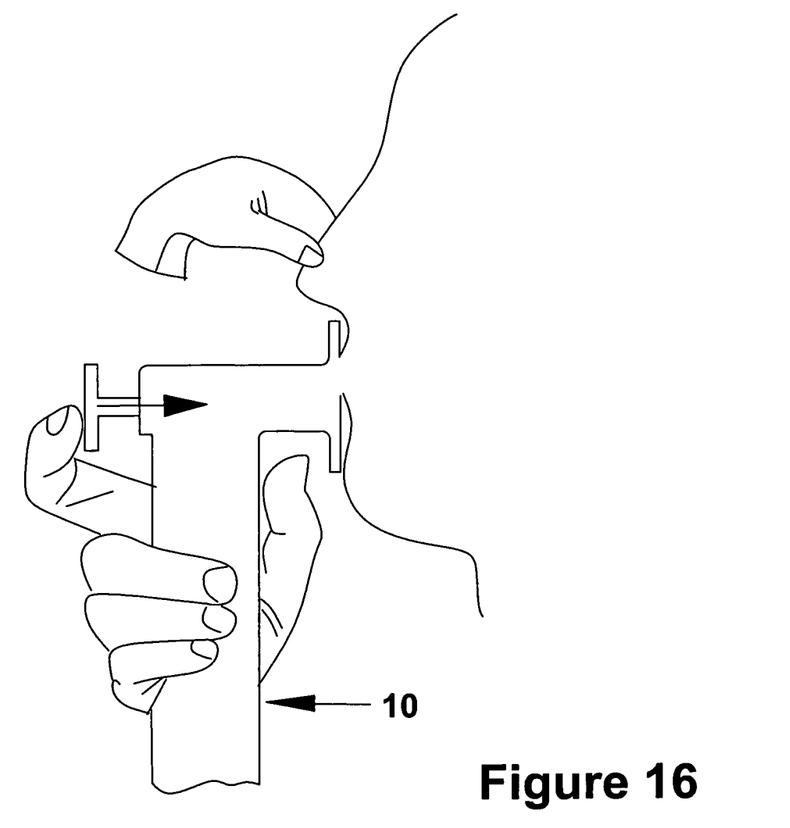
FIG. 16 is a view of a choking victim having inserted the device into his/her mouth and holding their nose with one hand, while beginning to actuate the knob of the spool with their other hand.
Figure 16A:
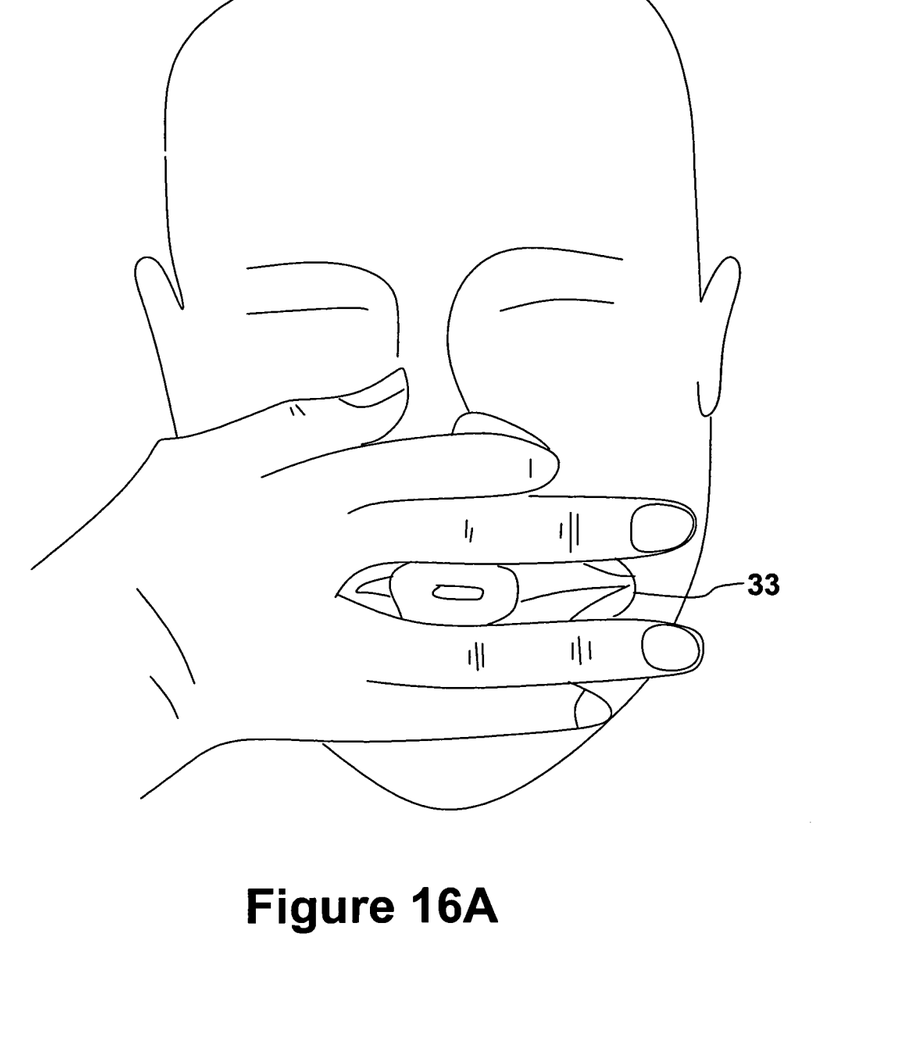
FIG. 16A illustrates an alternative technique for a choking victim to use the device on themselves, by utilize three of the five fingers of the one hand to maintain the mouthpiece within the mouth and throat by applying pressure to the sealing means, while the index finger and thumb of the same hand may pinch the victim's nose.

Although many choking victims may quickly become disoriented or even panic, once being unable to breathe freely, many other choking victims may nonetheless remain calm enough to utilize the device upon themselves, without the assistance of an aid-giver, as no one may be available at the time of the incident to render assistance. FIG. 16 illustrates a choking victim having inserted the device 10 into their own mouth, while holding their nose with one hand, and using their other hand to actuate the knob 63 to advance the spool 60 to dislodge the item. Alternatively, as seen in FIG. 16A, the choking victim may utilize three of the five fingers of the one hand to maintain the mouthpiece 25 within the mouth and throat by applying pressure to the sealing means 33, while the index finger and thumb of the one hand may pinch the victim's nose. Either of these techniques for operating the device may of course be utilized by a good samaritan seeking to provide assistance by utilizing the device on a victim.

Figure 17:
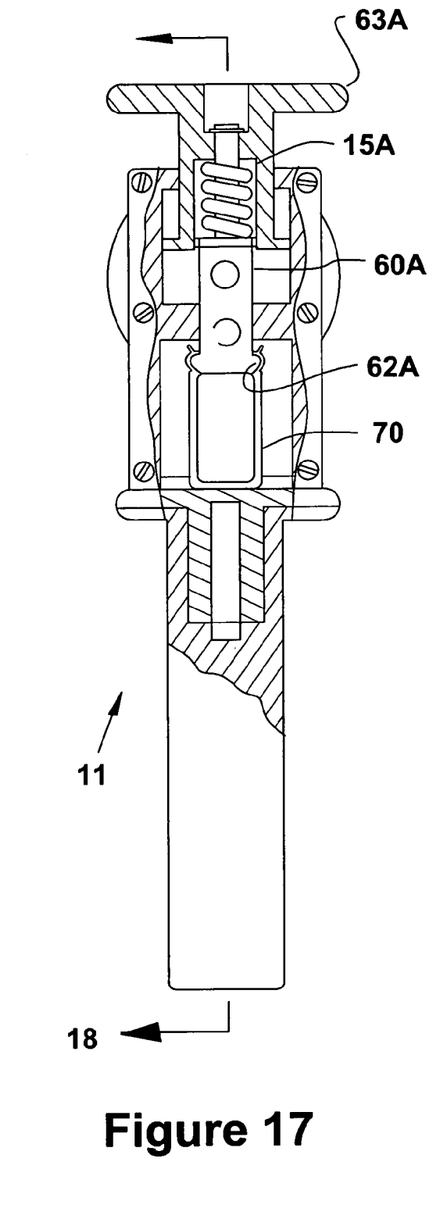
FIG. 17 is a side cross-sectional view through a second embodiment of the device of the present invention.

An alternate embodiment of the device 10 heretofore discussed is seen in FIGS. 17-18, and which may serve to assist the user of the current invention, whether it is the aid-giver or the victim seeking to perform dislodgment by themselves. This alternate embodiment 11 may be similar in configuration to the device 10, but may instead include a spool that is normally biased into the first position, where orifice 64 permits fluid communication between the first conduit 21 and the second conduit 22. This biasing may be countered, so as to permit the spool to be temporarily retained in the second position to allow the measured amount of vacuum pressure to be developed in the first conduit 21, through the engagement of a portion of spool 60A with spring clip 70 as follows.

Figures 19, 20, 21:
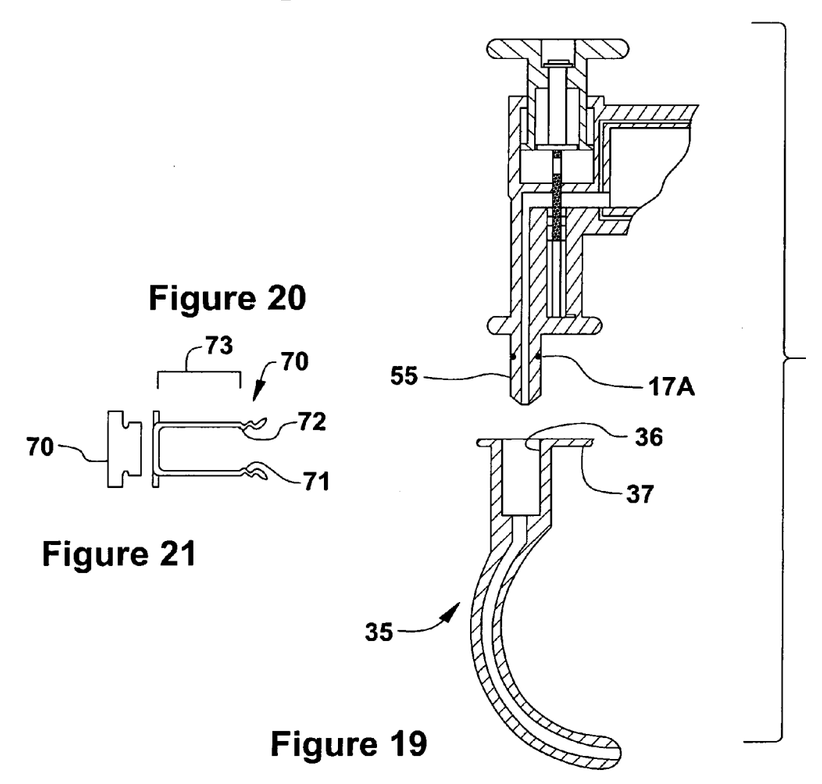
FIG. 19 is the cross-sectional view of FIG. 18, but with the removable mouthpiece detached from the governor portion of the device.
FIG. 20 is a cross-sectional view through the detent spring of the second embodiment shown in FIG. 17.
FIG. 21 is and end view of the spring clip of FIG. 20.
Figures 22, 23, 24:
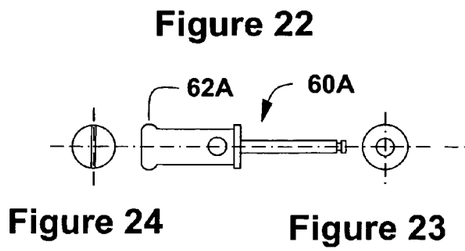
FIG. 22 is a side view of the spool of the second embodiment shown in FIG. 17.
FIG. 23 is a first end view of the spool of FIG. 22.
FIG. 24 is a second end view of the spool of FIG. 22.
Figure 25:
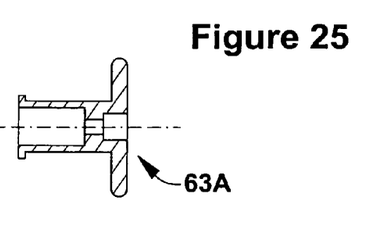
FIG. 25 is a cross-sectional view of the knob of the second embodiment shown in FIG. 17.

The spring clip 70 is seen in detail in FIGS. 20-21. The spring clip 70 may be disposed within the third conduit 23 between the second end 52 and the shoulder 53. The spool 60A is seen in detail in FIGS. 22-24, and as installed in FIGS. 17 and 18. Instead of the disk-shaped stop 62 found on the spool 60, spool 60A may comprise an annular protrusion 62A on the end of the spool opposite to the knob 63A, which in this embodiment may be a separate part that is mechanically fastened to the piston. The spring 15A may bias the spool to be in the first position, and the annular protrusion 62A of spool 60A may slide freely within the body 73 of the spring clip 70 as the piston 60A is moved by the user from the first position towards the second position. As the piston 60A approaches the second position, the annular protrusion 62A contacts an exterior portion 72 of the annular recess which bulges inward to block the free sliding motion of the spool. Upon application by the user of a slightly larger force to the spool, the spring clip 70 elastically deforms outward and thereafter permits engagement of the annular protrusion 62A within the annular recess 71 of the spring clip 70 to create a detent arrangement. The user may then release the force from the knob 63A, as the spring biasing is then countered by the detent.

The height of the exterior bulging portion 72 of the annular recess 71, and the material thickness and material type used for the spring clip 70 may be calibrated so as to provide an amount of engagement with the annular protrusion 62A of spool 60A that may be sufficient to counter the biasing of spring 15A, but which may not require application of a large force by the user to the knob 63A to disengage the protrusion from the recess. It may instead be preferable, particularly for the case where the user of the device is the victim, that a relatively small force be required to actuate the piston through contact with the knob.

Additionally, the device 10 and the device 11 may include a removable mouthpiece 35, as seen in FIG. 19. The mouthpiece 35 may comprise a female receptacle 36 that may receive a corresponding protrusion 55 on the governor portion 27 to permit replacement or cleaning of the mouthpiece, for hygienic reasons, after usage on a particular victim. Providing for a removable mouthpiece also enables the invention herein to support use of any one of a series of mouthpieces in assorted sizes, each of which may be tailored for the oropharangeal airway of a particular victim—ranging in size from the airway found on an infant to the airway of a professional football player. An O-ring 17A may be used to seal the joint, and prevent vacuum pressure losses between the mouthpiece 35 and protrusion 55. The O-ring 17 may be located in a recess on the protrusion 55, or in a recess within the receptacle 36. The mouthpiece may include a flange 37 to assist the user in mating the mouthpiece 35 onto the protrusion 55, which may be maintained thereon using a friction fit.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

TABLE I

Pressure Chamber Volume versus Piston Stroke (Piston Area = 1.53 in)

| STROKE | VOLUME- inches$^3$ | VOLUME- cm$^3$ (cc's) |
|--------|--------------------|-----------------------|
| 5      | 7.65               | 125                   |
| 6      | 9.18               | 150                   |
| 7      | 10.71              | 176                   |
| 8      | 12.24              | 201                   |
| 9      | 13.77              | 226                   |
| 10     | 15.30              | 251                   |
| 11     | 16.83              | 276                   |
| 12     | 18.36              | 301                   |

What is claimed is:

1. A suction device for vacuum removal of a lodged mass from the throat of a victim, said device comprising:
    a manifold, said manifold comprising first, second, and third conduits being in fluid communication with each other; said second conduit terminating in an outlet orifice in a mouthpiece portion of said manifold;
    a spool, said spool comprising an orifice, said spool being slidably disposed in said third conduit and moveable between a first position where said orifice permits fluid communication between said first conduit and said second conduit, and a second position where said spool blocks fluid communication therebetween;
    a piston, said piston being slidably disposed within said first conduit and moveable therein between a first end and a second end of said first conduit;
    a latch; said latch permitting said piston to be secured relative to said manifold at one or more discrete positions between said second end and said first end; and
    wherein when said spool is in said second position, and said piston is moved and latched to create a measured amount of vacuum pressure in said first conduit, said vacuum pressure being transmitted to said mouthpiece by moving said spool to said first position.

2. The suction device in accordance with claim 1, wherein said measured amount of vacuum pressure in said first chamber comprises vacuum pressure appropriate for use on a victim being in a size ranging between an infant-sized victim and a large adult-sized victim.

3. The suction device in accordance with claim 2, wherein said measured amount of vacuum pressure in said first chamber is created by moving said piston a corresponding stroke amount.

4. The suction device in accordance with claim 3, wherein said mouthpiece portion of said manifold comprises a removable mouthpiece.

5. The suction device in accordance with claim 4, wherein said removable mouthpiece permits replacement with a mouthpiece being appropriately sized for use in an oropharyngeal airway of a victim being in a size ranging between an infant-sized victim and a large adult-sized victim.

6. The suction device in accordance with claim 5, wherein said manifold comprises an orifice in an outer wall of said manifold into said first end of said first conduit; and wherein said piston is moveable in said first conduit using a portion of said piston protruding out of said manifold orifice.

7. The suction device in accordance with claim 6, wherein said second conduit has a first end and a second end, said outlet orifice in said mouthpiece being at said first end of said second conduit; and said second end of said second conduit interconnecting with said first conduit.

8. The suction device in accordance with claim 7, wherein said third conduit has a first end and a second end; said third conduit being transverse to said interconnection between said first and second conduits.

9. The suction device in accordance with claim 8, wherein said manifold comprises a second orifice in said outer wall, said second orifice being into said first end of said third conduit, said spool being movable using a portion of said spool protruding out of said second orifice.

10. The suction device in accordance with claim 9, wherein said piston comprises an O-ring seal to secure said vacuum pressure in said first conduit.

11. The suction device in accordance with claim 10, wherein said spool is spring biased.

12. The suction device in accordance with claim 11, wherein said spool is spring biased toward said second position; and wherein said spool is maintained in said first position by a spring clip engaging a portion of said spool.

13. The suction device in accordance with claim 12, wherein said spool comprises a knob on an end of said portion of said spool protruding out of said manifold orifice, said knob being usable for disengaging said spool from said spring clip to permit biasing of said piston from said second position to said first position.

14. The suction device in accordance with claim 13, wherein said latch comprises one or more tabs positioned on said piston, said one or more tabs being biased to protrude laterally; and wherein when said piston is moved said corresponding stroke amount, a last one of said one or more tabs having exited said manifold orifice of said first conduit engages said manifold.

15. The suction device in accordance with claim 13, wherein said latch comprises a series of holes on said piston, and a spring biased rocker arm pivotally attached to said manifold to be in line with said series of piston holes; and wherein when said piston is moved said corresponding stroke amount, said rocker arm engages a last one of said holes having exited said manifold orifice of said first conduit.

16. The suction device in accordance with claim 15, wherein each of said series of holes is correspondingly labeled, said corresponding label identifying each hole in said series as being for said measured amount of vacuum pressure for said victim size.

17. A vacuum device for use in the removal of a lodged mass from the throat of a victim, said device comprising:
a manifold, said manifold comprising first, second, and third conduits being in selective fluid communication with each other;
a mouthpiece, said mouthpiece comprising a conduit having a first end terminating in an outlet orifice and a second end, said mouthpiece being connected to said manifold with said second end of said mouthpiece conduit being in fluid communication with said second conduit;
a spool, said spool providing said selective fluid communication by being slidably disposed in said third conduit and moveable between a first position where an orifice in said spool permits fluid communication between said first and second conduits, and a second position where said spool blocks fluid communication therebetween;
a piston, said piston being slidably disposed within said first conduit and moveable therein between a first end and a second end of said first conduit;
a latch; said latch permitting said piston to be secured relative to said manifold at one or more positions; and
wherein when said spool is in said second position, and said piston is moved and latched to create an appropriate amount of vacuum pressure in said first conduit, said vacuum pressure is transmitted to said mouthpiece by moving said spool to said first position.

18. The suction device in accordance with claim 17, wherein said appropriate amount of vacuum pressure in said first chamber comprises vacuum pressure safe for use on a victim being in a size ranging between an infant-sized victim and a large adult-sized victim.

19. The suction device in accordance with claim 17, wherein said appropriate amount of vacuum pressure in said first chamber is created by moving said piston a corresponding stroke amount.

20. The suction device in accordance with claim 17, wherein said mouthpiece comprises a removable mouthpiece; and wherein said removable mouthpiece permits replacement with a mouthpiece being appropriately sized for use in an oropharyngeal airway of a victim being in a size ranging between an infant-sized victim and a large adult-sized victim.

21. The suction device in accordance with claim 17, wherein said spool is spring biased toward said second position; and wherein said spool is maintained in said first position by a spring clip engaging a portion of said spool.

22. The suction device in accordance with claim 21, wherein said spool comprises a knob on an end of said portion of said spool protruding out of said manifold orifice, said knob being usable for disengaging said spool from said spring clip to permit biasing of said piston from said second position to said first position.

23. The suction device in accordance with claim 17, wherein said latch comprises one or more tabs positioned on said piston, said one or more tabs being biased to protrude laterally; and wherein when said piston is moved said corresponding stroke amount, a last one of said one or more tabs having exited said manifold orifice of said first conduit engages said manifold.

24. The suction device in accordance with claim 17, wherein said latch comprises a series of holes on said piston, and a spring biased rocker arm pivotally attached to said manifold to be in line with said series of piston holes; and wherein when said piston is moved said corresponding stroke amount, said rocker arm engages a last one of said holes having exited said manifold orifice of said first conduit.

25. The suction device in accordance with claim 24, wherein each of said series of holes is correspondingly labeled, said corresponding label identifying each hole in said series as being for said measured amount of vacuum pressure for said victim size.

* * * * *